US012667567B2

(12) United States Patent
Kador et al.

(10) Patent No.: US 12,667,567 B2
(45) Date of Patent: Jun. 30, 2026

(54) METHOD OF PREVENTING BLAST-INDUCED LOSS OF COCHLEAR AND VESTIBULAR HAIR CELLS AND AUDITORY SPIRAL GANGLION NEURONS

(71) Applicant: Therapeutic Vision, Inc., Omaha, NE (US)

(72) Inventors: Peter Fritz Kador, Meredith, NH (US); Richard Salvi, Mount Dora, FL (US)

(73) Assignee: Therapeutic Vision, Inc., Omaha, NE (US)

( * ) Notice: Subject to any disclaimer, the term of this patent is extended or adjusted under 35 U.S.C. 154(b) by 0 days.

(21) Appl. No.: 19/225,092

(22) Filed: Jun. 2, 2025

(65) Prior Publication Data

US 2025/0352545 A1    Nov. 20, 2025

Related U.S. Application Data

(63) Continuation of application No. 19/213,544, filed on May 20, 2025, now abandoned.

(60) Provisional application No. 63/666,729, filed on Jul. 2, 2024, provisional application No. 63/649,881, filed on May 20, 2024.

(51) Int. Cl.
| | |
|---|---|
| *A61K 31/506* | (2006.01) |
| *A61K 9/00* | (2006.01) |
| *A61P 27/16* | (2006.01) |

(52) U.S. Cl.
CPC .......... *A61K 31/506* (2013.01); *A61K 9/0053* (2013.01); *A61P 27/16* (2018.01)

(58) Field of Classification Search
CPC ...... A61K 31/506; A61K 9/0053; A61P 27/16
See application file for complete search history.

(56) References Cited

PUBLICATIONS

Escabi CD, et al. J Acoust Soc Am. Nov. 2019;146(5):3692. (Year: 2019).*
IIADRP; "Effect of Multifunctional Redox Modulator (MFRM) HK-2 on Acoustic Blast Overpressure and Cognitive Function"; listed as a project on IADRP site, accessed Mar. 19, 2024.

NIH Report—Reporter; "Effect of Multifunctional Redox Modulator (MFRM) HK-2 on Acoustic Blast Overpressure and Cognitive Function", project summary on NIH, accessed Mar. 19, 2024.
Kador, P. F. et al, "Multifunctional Redox Modulators Protect Auditory, Visual, and Cognitive Function"; Antioxid Redox Signal. Jun. 2022; 36(16-18): 1136-1157. Published online Jun. 3, 2022. doi: 10.1089/ars.2021.0129.
Chen, G.D., et al., "Novel Oral Multifunctional Antioxidant Prevents Noise-Induced Hearing Loss and Hair Cell Loss"; Hear Res. Author manuscript; available in PMC Mar. 15, 2021. Published in final edited form as: Hear Res. Mar. 15, 2020; 388: 107880. Published online Jan. 3, 2020. doi: 10.1016/j.heares.2019.107880.
Levy, J., "Preserving Precious Hearing: The Benefits of Ear Plugs in Noise Reduction"; website article, By Admin, Feb. 13, 2023, Last Updated on Jul. 11, 2023 by Admin.
Gan, R. Z., et al., "Characterization of Protection Mechanisms to Blast Overpressure for Personal Hearing Protection Devices—Biomechanical Measurement and Computational Modeling"; Military Medicine, vol. 184, Issue Supplement_1, Mar.-Apr. 2019, pp. 251-260, https://doi.org/10.1093/milmed/usy299; Published: Mar. 21, 2019.
Daszynski, D., "Ocular, Neural, and Cellular Biodistribution of Multifunctional Antioxidants"; University of Nebraska Medical Center, Theses and Dissertations, Spring May 9, 2020 (dicloses both HK-2 and acoustic blast overpressure (ABO), noise-induced hearing loss (NIHL) and the oral administration of the MFAO HK-2, but no ear plugs; 283 page pdf direct link).
Ewert D.L., et al., Antioxidant treatment reduces blast-induced cochlear damage and hearing loss. Hear Res, 2012. 285(1-2): p. 29-39. (Abstract and Highlights).
Fang, Z., et al., Biomarkers of Oxidative Stress and Endogenous Antioxidants for Patients with Chronic Subjective Dizziness. Sci Rep, 2020. 10(1): p. 1478.
Ozbay, I., et al., Serum prolidase, malondialdehyde and catalase levels for the evaluation of oxidative stress in patients with peripheral vertigo. Eur Arch Otorhinolaryngol, 2021. 278(10): p. 3773-3776. (Abstract).
Gucluturk, M.T., et al., The Role of Oxidative Stress and Inflammatory Mediators in Benign Paroxysmal Positional Vertigo. J Int Adv Otol, 2016. 12(1): p. 101-5.

* cited by examiner

*Primary Examiner* — James H Alstrum-Acevedo
*Assistant Examiner* — Manahil Mirghani Ali Abdalhameed
(74) *Attorney, Agent, or Firm* — Nath, Goldberg & Meyer; Joshua B. Goldberg

(57) ABSTRACT

A method of preventing blast-induced loss of cochlear and vestibular hair cells and auditory spiral ganglion neurons including orally administering a composition comprising HK-2 to a subject in need thereof. The subject may be a subject at increased risk of exposure to an acoustic blast wave, or a subject that has already been exposed to an acoustic blast wave.

15 Claims, 10 Drawing Sheets

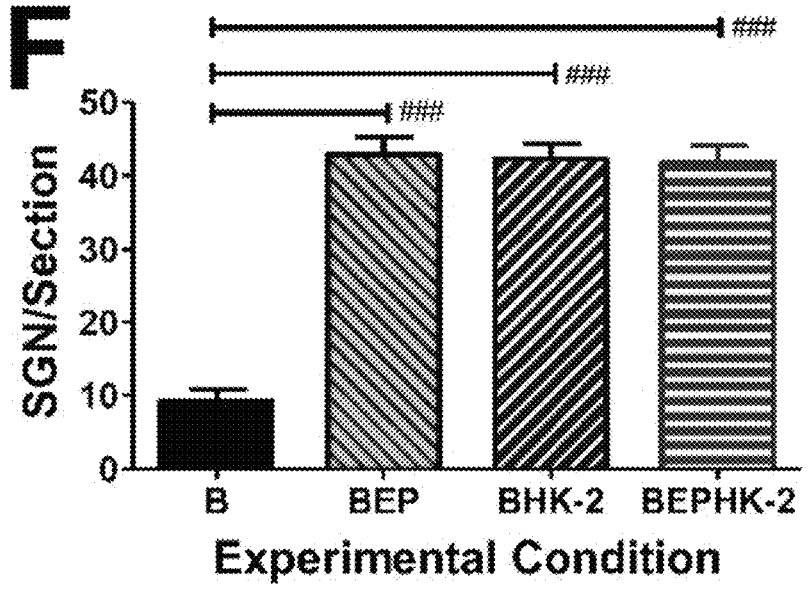
*FIG. 4F*
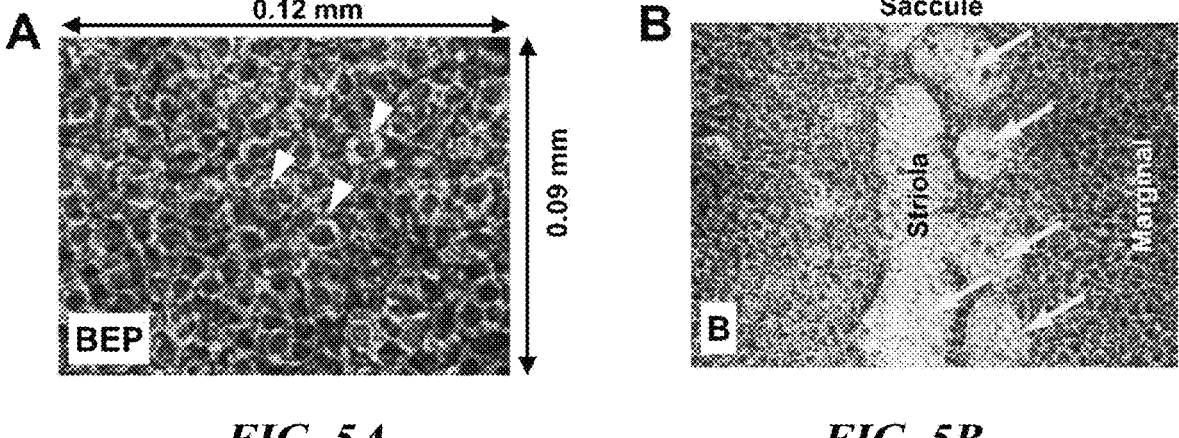
*FIG. 5A*          *FIG. 5B*

A

B

C

1

METHOD OF PREVENTING BLAST-INDUCED LOSS OF COCHLEAR AND VESTIBULAR HAIR CELLS AND AUDITORY SPIRAL GANGLION NEURONS

CROSS-REFERENCE TO RELATED APPLICATIONS

This application is a continuation of U.S. patent application Ser. No. 19/213,544, filed on May 20, 2025, which claims the benefit of U.S. Provisional Patent Application No. 63/649,881, filed on May 20, 2024 and the benefit of U.S. Provisional Patent Application No. 63/666,729, filed on Jul. 2, 2024, the entire contents of each of which are incorporated herein by reference.

FIELD AND BACKGROUND OF THE INVENTION

The disclosure of the present patent application relates to method of preventing blast-induced hearing loss, and particularly to a method of preventing blast-induced loss of cochlear and vestibular hair cells and auditor spiral ganglion neurons.

DESCRIPTION OF THE PRIOR ART

In industrialized societies, noise is ubiquitous and a major cause of hearing loss among the young and middle aged. (Carroll, Y. I., et al., *Vital Signs: Noise-Induced Hearing Loss Among Adults*—United States 2011-2012. MMWR Morb Mortal Wkly Rep, 2017. 66(5): p. 139-144; Nelson, D. I., et al., *The global burden of occupational noise-induced hearing loss*. Am J Ind Med, 2005. 48(6): p. 446-58.) Noise-induced hearing loss (NIHL), together with tinnitus and hyperacusis comorbidities, are extremely common among military personnel exposed to continuous, impulse or blast wave noise. (Helfer, T. M., et al., *Noise-induced hearing injury and comorbidities among postdeployment U.S. Army soldiers*: April 2003-June 2009. Am J Audiol, 2011. 20(1): p. 33-41; Orru, H., et al., *Hearing loss among military personnel in relation to occupational and leisure noise exposure and usage of personal protective equipment*. Noise Health, 2020. 22(107): p. 90-98; Zaugg, T. L., et al., *Subjective Reports of Trouble Tolerating Sound in Daily Life versus Loudness Discomfort Levels*. Am J Audiol, 2016. 25(4): p. 359-363.) Hearing protection (e.g., earplugs/ear muffs), when worn properly, reduces the risk of NIHL. (Samelli, A. G., et al., *The study of attenuation levels and the comfort of earplugs*. Noise Health, 2018. 20(94): p. 112-119.) However, hearing protection is seldom worn in front line combat or places where situational awareness and/or auditory communication are critical (e.g., emergency responders, call center operators). (Westcott, M., *Acoustic shock injury (ASI)*. Acta Otolaryngol Suppl, 2006(556): p. 54-8.) In many situations, explosions and gun fire occur unexpectedly before hearing protection can be deployed. (Westcott, M.; Budak, B., K. Coban, and S. S. Erbek, *Evaluation of the hearing status in carpenters*. Int Arch Occup Environ Health, 2021. 94(7): p. 1703-1707.)

Advances in understanding the biological bases of NIHL have led to pharmacologic efforts to reduce the risk of hearing losses induced mainly by the generation of free radicals and oxidative stress. (Kim, Y. R., et al., *Galangin prevents aminoglycoside-induced ototoxicity by decreasing mitochondrial production of reactive oxygen species in mouse cochlear cultures*. Toxicol Lett, 2016. 245: p. 78-85; Ding, D., et al., *N-acetyl-cysteine prevents age-related hearing loss and the progressive loss of inner hair cells in gamma-glutamyl transferase 1 deficient mice*. Aging (Albany NY), 2016. 8(4): p. 730-50; Tavanai, E. and G. Mohammadkhani, *Role of antioxidants in prevention of age-related hearing loss: a review of literature*. Eur Arch Otorhinolaryngol, 2017. 274(4): p. 1821-1834; Yamasoba, T., et al., *Current concepts in age-related hearing loss: epidemiology and mechanistic pathways*. Hear Res, 2013. 303: p. 30-8; Henderson, D., et al., *The role of oxidative stress in noise-induced hearing loss*. Ear Hear, 2006.27(1): p. 1-19; Minami, S. B., et al., *Creatine and tempol attenuate noise-induced hearing loss*. Brain Res, 2007. 1148: p. 83-9.) Free radical levels reportedly increase in marginal cells of the stria vascularis minutes to hours following intense noise exposure. (Yamane, H., et al., *The emergence of free radicals after acoustic trauma and strial blood flow*. Acta Otolaryngol Suppl, 1995. 519: p. 87-92.) Because this early rise in oxidative stress occurs prior to significant hair cell loss, hearing loss was thought to result from other factors besides oxidative stress. However, subsequent research revealed a gradual and prolonged buildup of free radical induced oxidative stress in the organ of *Corti* and hair cells with levels peaking 7-10 days post-exposure followed by a decline. (Yamashita, D., et al., *Delayed production of free radicals following noise exposure*. Brain Res, 2004. 1019 (1-2): p. 201-9.) While the increase in free radicals is associated with hair cell degeneration, it is unclear if excess oxidative stress plays a major role in spiral ganglion neuron (SGN) degeneration.

Recently, we investigated whether HK-2 (1-(5-hydroxy-pyrimidin-2-yl) pyrrolidine-2,5-dione), a novel multifunctional redox modulator (MFRM), could protect against NIHL. HK-2, which crosses the blood-brain barrier, not only scavenges free radicals, but also prevents the generation of these highly toxic radicals. (Kador, P. F. and R. Salvi, *Multifunctional Redox Modulators Protect Auditory, Visual, and Cognitive Function*. Antioxid Redox Signal, 2021. 36(16-18): p. 1136-57.) When control rats were exposed to 95 dB SPL octave band noise, 8 h/d for 21 days, they developed moderate, mid-frequency hearing loss and moderate outer hair cell (OHC) loss. (Chen, G. D., et al., *Novel oral multifunctional antioxidant prevents noise-induced hearing loss and hair cell loss*. Hear Res, 2020. 388: p. 107880.) However, if noise-exposed rats were treated with HK-2 before, during and after the exposure, both the hearing loss and hair cell loss were significantly reduced in a dose-dependent manner. A recent report also found that antioxidant therapy protected against a blast wave exposure that caused moderate hearing loss and hair cell loss. (Ewert, D. L., et al., *Antioxidant treatment reduces blast-induced cochlear damage and hearing loss*. Hear Res, 2012. 285(1-2): p. 29-39.)

Because blast-induced hearing damage has been reported to stem mainly from direct mechanical damage to the cochlea rather than generated oxidative stress (Hamernik, R. P., et al., *Anatomical correlates of impulse noise-induced mechanical damage in the cochlea*. Hear Res, 1984. 13(3): p. 229-47), therapies targeting oxidative stress might be expected to prove ineffective against blast-induced mechanical damage to the cochlea.

Intense blast wave exposures can cause dizziness and balance problems, conditions associated with damage to the peripheral vestibular system. Hair cells in the otolithic balance organs, the saccule and utricle, are believed to be more vulnerable to blast wave exposure than hair cells located in the ampullae of the semicircular canals. (Akin, F. W., et al., *Vestibular consequences of mild traumatic brain injury and blast exposure: a review*. Brain Inj, 2017. 31(9): p. 1188-1194.) However, persistent damage to hair cell stereocilia has been observed in the cristae in the semicircular canals as well as in the utricle and saccule. Vestibular hair cell damage has been linked to behavioral vestibular deficits and abnormal vestibular-evoked eye movements. (Lien, S. and J. D. Dickman, *Vestibular Injury After Low-Intensity Blast Exposure*. Front Neurol, 2018. 9: p. 297.) Some reports suggest that vestibular disorders and vestibulotoxicity result from elevated levels of oxidative stress. (Fang, Z., et al., *Biomarkers of Oxidative Stress and Endogenous Antioxidants for Patients with Chronic Subjective Dizziness*. Sci Rep, 2020. 10(1): p. 1478; Ozbay, I., et al., *Serum prolidase, malondialdehyde and catalase levels for the evaluation of oxidative stress in patients with peripheral vertigo*. Eur Arch Otorhinolaryngol, 2021. 278(10): p. 3773-3776; Gucluturk, M. T., et al., *The Role of Oxidative Stress and Inflammatory Mediators in Benign Paroxysmal Positional Vertigo*. J Int Adv Otol, 2016. 12(1): p. 101-5.)

Exposure to intense blasts can cause direct mechanical damage to cochlear hair cells, support cells and auditory nerve fibers that synapse on the hair cells. (Hamernik, R. P., et al., *Anatomical correlates of impulse noise-induced mechanical damage in the cochlea*. Hear Res, 1984. 13(3): p. 229-47; Kim, J., et al., *Osmotic stabilization prevents cochlear synaptopathy after blast trauma*. Proc Natl Acad Sci USA, 2018. 115(21): p. E4853-E4860; Cho, S. I., et al., *Mechanisms of hearing loss after blast injury to the ear*. PLoS One, 2013. 8(7): p. e67618.) These observations suggested that HK-2, a multifunctional redox modulator, might provide little or no protection against blast induced-mechanical damage to cochlear hair cells and neurons. However, blast-induced hearing loss likely involves multiple mechanisms such as neuroinflammation, excitotoxicity, toxic mixing of endolymph and perilymph, and disruption of the blood-labyrinth barrier, factors likely to contribute to oxidative stress. (Cho, S. I. et al.; Bohne, B. A. and G. W. Harding, *Degeneration in the cochlea after noise damage: primary versus secondary events*. Am J Otol, 2000. 21(4): p. 505-9; Frye, M. D., A. F. Ryan, and A. Kurabi, *Inflammation associated with noise-induced hearing loss*. J Acoust Soc Am, 2019. 146(5): p. 4020.) Combination antioxidant therapy was shown to greatly reduce temporary and permanent blast-induced hearing loss and OHC loss suggesting that the therapy protected against both the mechanical and metabolic aspects of the exposure. (Ewert, D. L. et al.; Choi, C. H., *Mechanisms and treatment of blast induced hearing loss*. Korean J Audiol, 2012. 16(3): p. 103-7.)

Thus, a method of preventing blast-induced loss of cochlear and vestibular hair cells and auditor spiral ganglion neurons solving the aforementioned problems is desired.

SUMMARY OF THE INVENTION

A method of preventing blast-induced hearing loss comprising daily administration of 1-(5-hydroxy-2-pyrimidyl) pyrrolidine-2,5-dione (HK-2) is disclosed. In an embodiment, the HK-2 may be administered to a subject at increased risk of exposure to a blast-wave. In a further embodiment, the HK-2 may be administered to a subject after exposure to a blast-wave. In an embodiment, the method comprises prevention of one or more of loss of cochlear hair cells, loss of vestibular hair cells, and loss of auditor spiral ganglion neurons. In an embodiment, the HK-2 may be administered daily for at least 30 days. In an embodiment the HK-2 may be administered in a dose of about 50 mg per kg weight per day.

These and other features of the present subject matter will become readily apparent upon further review of the following specification.

BRIEF DESCRIPTION OF DRAWINGS

FIG. 4F shows a graph comparing the SGN loss in blast exposed rats (B) to the ANF loss in blast exposed rats fitted with earplugs (BEP), treated with HK-2 (BHK-2), and fitted with earplugs and treated with HK-2 (BEPHK-2).

FIG. 5A shows quantification of vestibular hair cells in a blast exposed rat protected with earplugs.

FIG. 5B shows quantification of vestibular hair cells in an unprotected blast exposed rat.

5

6

Figure 1A:
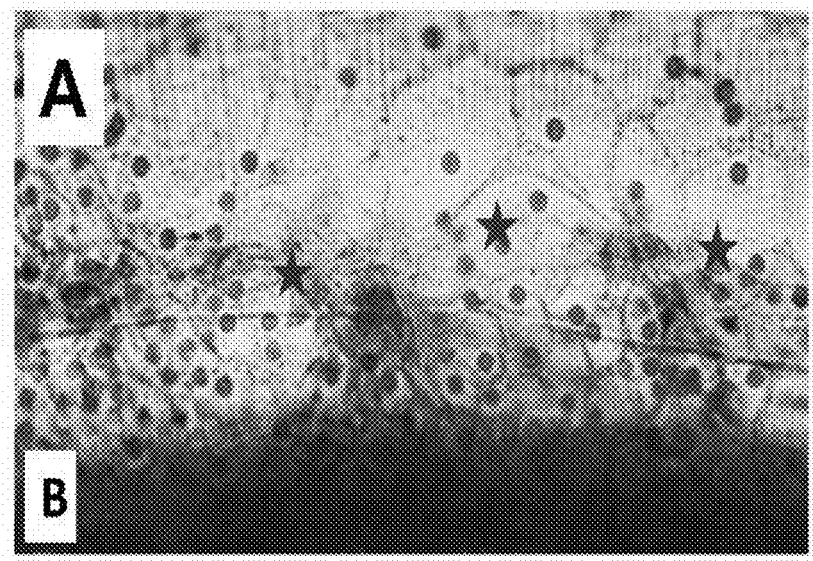
FIG. 1A depicts a representative photomicrograph of a surface preparation taken from the middle of the basal turn of the cochlea of an untreated, blast exposed rat.

Similar reference characters denote corresponding features consistently throughout the attached drawings.

DETAILED DESCRIPTION

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Methods of Preventing Hearing Associated Injuries Resulting from Blast Wave Exposure Blast wave exposure, a leading cause of hearing loss and balance dysfunction among military personnel, arises primarily from direct mechanical damage to the mechanosensory hair cells and supporting structures or indirectly through excessive oxidative stress. We previously reported that HK-2, an orally active, multifunctional redox modulator, was highly effective in reducing both hearing loss and hair cells loss in rats exposed to a moderate intensity workday noise that likely damages the cochlea primarily from oxidative stress versus direct mechanical trauma. To determine if HK-2 could also protect cochlear and vestibular cells from damage caused primarily from direct blast-induced mechanical trauma versus oxidative stress, we exposed rats to six blasts of 186 dB peak SPL. The rats were divided into four groups: (B) blast alone, (BEP) blast plus earplugs, (BHK-2) blast plus HK-2 and (BEPHK-2) blast plus earplugs plus HK-2. HK-2 was orally administered at 50 mg/kg/d from 7-days before to 30-day after the blast exposure. Cochlear and vestibular tissues were harvested 60-d post-exposure and evaluated for loss of outer hair cells (OHC), inner hair cells (IHC), auditory nerve fibers (ANF), spiral ganglion neurons (SGN) and vestibular hair cells in the saccule, utricle and semicircular canals. In the untreated blast-exposed group (B), massive losses occurred to OHC, IHC, ANF, SGN and only the vestibular hair cells in the striola region of the saccule. In contrast, rats treated with HK-2 (BHK-2 group) sustained significantly less OHC (67%) and IHC (57%) loss compared to the B group. Importantly, HK-2 completely prevented ANF, SGN and saccule hair cell loss. There was no loss of ANF, SGN or saccular hair cells in the BEP and BEPHK-2 groups; however, OHC and IHC losses in these two groups were significantly less than in the BHK-2 group. Thus, HK-2 not only ameliorated OHC and IHC loss, but also completely prevented loss of ANF, SGN and saccule hair cells. The powerful protective effects of this oral MFRM make HK-2 an extremely promising candidate for human clinical trials.

Based on our earlier reports and those of others, studies were conducted to determine if HK-2 could reduce blast wave induced injury to the cochlea and peripheral vestibular system. We exposed four groups of rats to six blast waves at 5 minute intervals (186 dB peak SPL) and compared the amount of cochlear and vestibular hair cell loss and the degree of cochlear neuronal damage in a (1) blast exposed group (B), (2) a blast exposed group treated with earplugs (BEP), (3) a blast exposed group treated with HK-2 (BHK-2) and (4) a blast exposed group treated with both earplugs and HK-2 (BEPHK-2).

A method of preventing blast-induced hearing loss comprising daily administration of 1-(5-hydroxy-2-pyrimidyl) pyrrolidine-2,5-dione (HK-2) is disclosed. In an embodiment, the HK-2 may be administered to a subject at increased risk of exposure to a blast-wave. In a further embodiment, the HK-2 may be administered to a subject after exposure to a blast-wave. In an embodiment, the method comprises prevention of one or more of loss of cochlear hair cells, loss of vestibular hair cells, and loss of auditor spiral ganglion neurons. In an embodiment, the HK-2 may be administered daily for at least 30 days. In an embodiment the HK-2 may be administered in a dose of about 50 mg per kg weight per day.

Figure 2A:
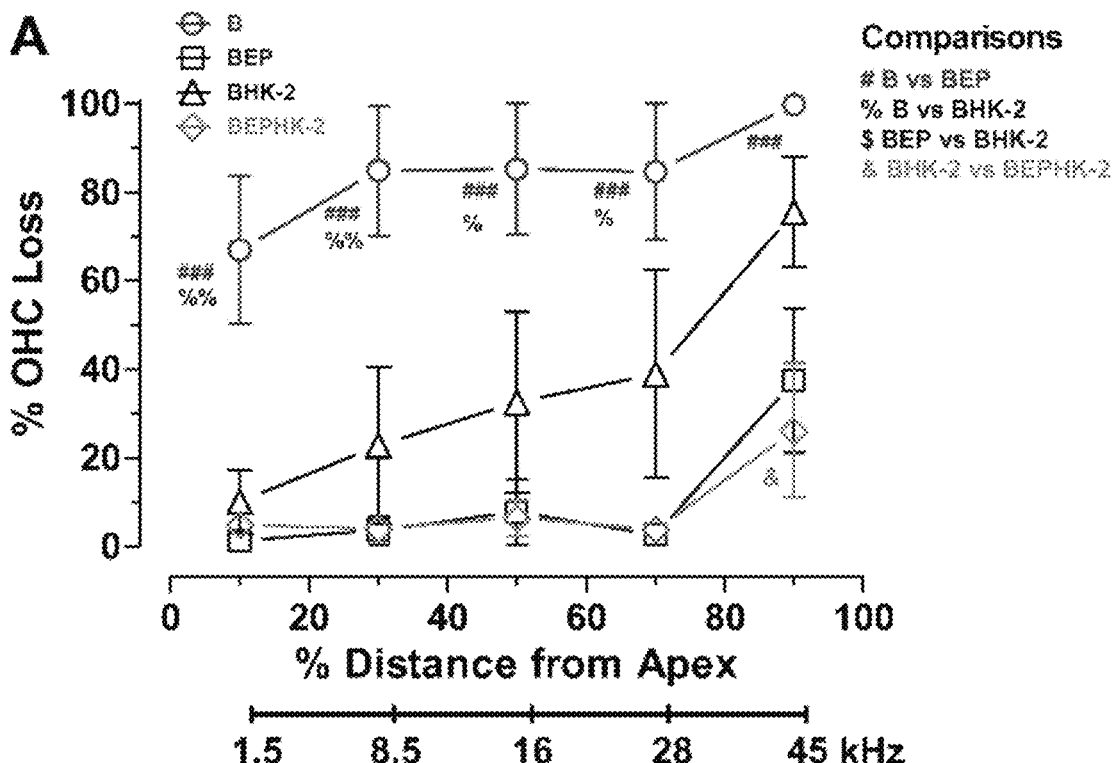
FIG. 2A depicts a graph illustrating total outer hair cell (OHC) loss in blast exposed rats fitted with earplugs (BEP), treated with HK-2 (BHK-2), and fitted with earplugs and treated with HK-2 (BEPHK-2).
Figure 2B:
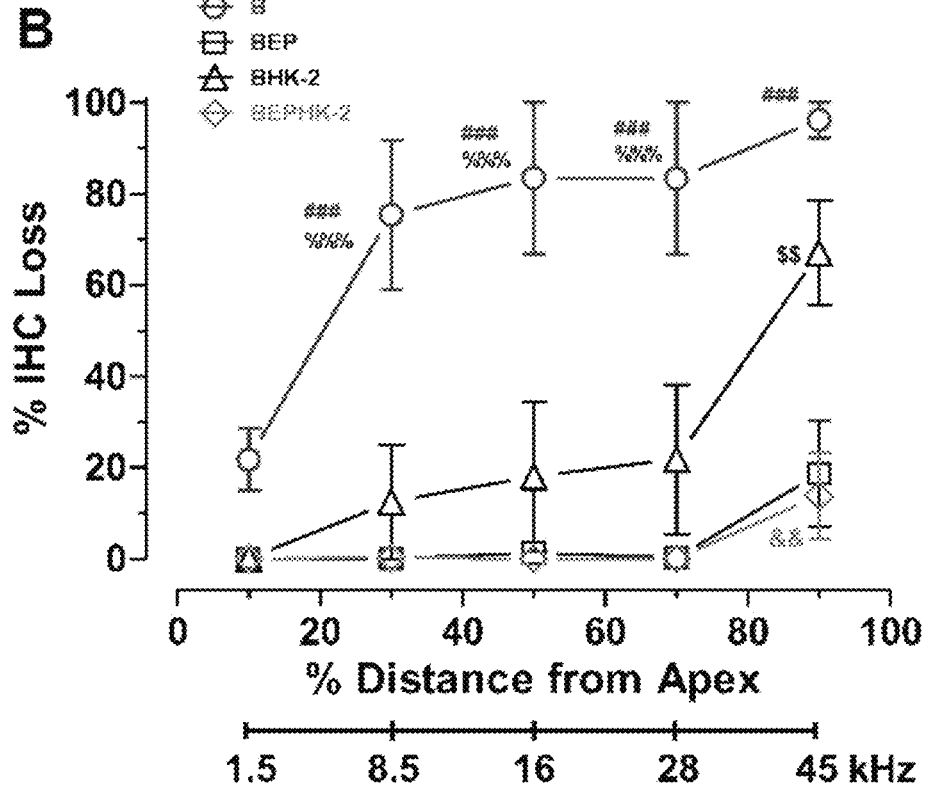
FIG. 2B depicts a graph illustrating total inner hair cell (JHC) loss in blast exposed rats fitted with earplugs (BEP), treated with HK-2 (BHK-2), and fitted with earplugs and treated with HK-2 (BEPHK-2).

Cochlear hair cell loss: Our results provide compelling evidence that HK-2, a MFRM, provides significant protection against blast-induced destruction of OHC, IHC, ANF and SGN. Treatment with HK-2 reduced total OHC loss by ~67% and total IHC loss by ~57.3%. HK-2 was least effective in preventing OHC and IHC loss in the most basal part of the cochlea where the blast-induced lesion was nearly 100% (FIG. 2A). The massive loss of OHC and IHC in the extreme base of the cochlea was likely the result of immediate and direct mechanical destruction of the sensory epithelium as described previously. (Hamernik, R. P. et al.) However, HK-2 provided significant protection of OHC and IHC in the apical three-fourths of the cochlea where OHC and IHC losses were 80% or less (FIG. 2A-2B). Earplugs provided nearly complete protection against blast-induced OHC and IHC loss except in the most basal segment of the cochlea where ~40% of OHC and ~20% of IHC were missing. The OHC and IHC lesions in this region are most likely caused by direct mechanical destruction of the organ of Corti because combining HK-2 with earplugs did not significantly reduce the hair cells lesions compared to earplugs alone (squares versus diamond symbols, FIG. 2A-2B). These results suggest that HK-2 does not protect against direct mechanical damage to hair cells.

HK-2 was not as effective as earplugs at preventing blast-induced OHC or IHC loss. If this difference is due to metabolic rather than mechanical factors, then we can speculate on possible reasons for this. One possibility is that the dose of HK-2 used in this study was too low to completely eliminate all blast-induced oxidative stress. This hypothesis could be tested by conducting a dose-response study to identify the most effective dose. An alternative explanation is that oxidative stress is one of several biological mechanisms that contributes to blast-induced hair cell death. Many other factors such as neuroinflammation, excitotoxicity, and neurovascular impairment could be involved in NIHL and therapeutic interventions in combination with HK-2 could be tested to assess their efficacy.

Auditory nerve fibers and spiral ganglion: Our analysis focused on ANF and SGN degeneration in the middle of the basal turn of the cochlea near the 25 kHz region of the cochlea. The blast exposure caused a massive loss of ANF (FIG. 3F) and SGN (FIG. 4F) relative to the earplug group (BEP). Approximately 89% of the ANF and 79% of the SGN were destroyed by the blast exposure (re the EP group). Treatment with HK-2 restored ANF to essentially normal levels (~8-fold increase) and SGN to essentially normal values (~3.7-fold increase). Thus, HK-2 provided complete protection of ANF and SGN in the 25 kHz region of the cochlea whereas the drug provided only partial protection of OHC and IHC in this region. While the evidence for "complete" protection is impressive, these results should be interpreted cautiously given that ANF and SGN degeneration may occur over many months or years depending on the species. (Yu, Q., et al., *Protection of spiral ganglion neurons from degeneration using small-molecule TrkB receptor agonists*. J Neurosci, 2013. 33(32): p. 13042-52.) Some NIHL studies suggest that IHC are required for SGN survival; however, more recent findings in genetic mutants demonstrate that SGN can survive in the absence of IHC. (Zilberstein, Y., M. C. Liberman, and G. Corfas, *Inner hair cells are not required for survival of spiral ganglion neurons in the adult cochlea*. J Neurosci, 2012. 32(2): p. 405-10.) The authors suggested that SGN loss following noise exposure may be caused by delayed metabolic secondary damage to ANF or SGN. If so, then HK-2 would appear to have neuroprotective effects, consistent with previous studies showing that HK-2 is neuroprotective in other systems. (Kador and Salvi 2021). These results suggest a novel use of HK-2, namely preventing the degeneration of ANF and SGN in cochlear implant patients. One important question that remains to be answered is how long the neuroprotective effects of HK-2 lasts. We administered HK-2 for 30 days following the blast exposure and harvested the tissues 60 days post-exposure. If the ANF and SGN were to degenerate at much longer survival times, this would suggest that there is a prolonged period of oxidative stress following the blast exposure. If no further degeneration occurred at much longer survival time, then one might conclude that a heightened period of oxidative stress mainly occurs 30 days or less following the blast exposure. Future experiments in which the duration or timing of HK-2 treatment is varied would help to resolve these questions.

Figure 5C:
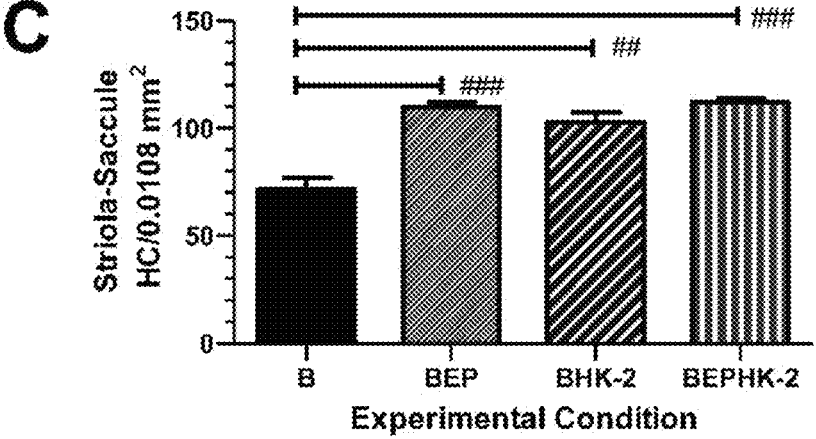
FIG. 5C depicts a graph illustrating damage to the Striola-Saccule under various experimental conditions.
Figure 5D:
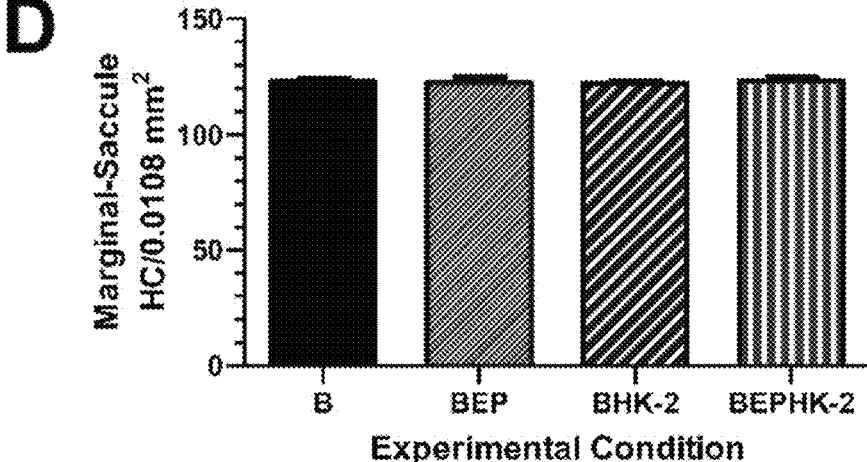
FIG. 5D depicts a graph illustrating damage to the Marginal-Saccule under various experimental conditions.

HK-2 protects utricular hair cells in the striola: Some studies suggest that blast exposures damage the stereocilia on vestibular hair cells while others have failed to observe vestibular hair cell loss. (Mao, B., et al., *Assessment of auditory and vestibular damage in a mouse model after single and triple blast exposures*. Hear Res, 2021. 407: p. 108292.) Our results clearly show that six blasts of 186 dB pSPL selectively destroyed hair cells in the macula of the saccule, but only in the striola region (FIG. 5B-5C), but not the marginal zone (FIG. 5B, 5D). There was no evidence of hair cell loss in either the striola or marginal zones of the macula of the utricle (FIG. 6A-6B) and no evidence of hair cell loss in the crista of the ampulla in the three semicircular canals. The enhanced vulnerability of saccular hair cells in striola region relative to hair cells in the utricle and semicircular canals is likely related to its closer proximity to the stapes which transmits pressure fluctuation not only to the cochlea, but also the saccule, consistent with the observation that saccular afferent nerve fibers respond to sound. (McCue, M. P. and J. J. Guinan, Jr., *Acoustically responsive fibers in the vestibular nerve of the cat*. J Neurosci, 1994. 14(10): p. 6058-70.) It is unclear from our results why hair cells in the striola region of the macula of the saccule are more susceptible to blast trauma than those in the marginal region. Sensitivity to blast trauma could be related to regional differences in stereocilia bundle length, stiffness, and sensitivity and the magnitude of the forces applied to the hair cell lining the macula. (Howard, J. and J. F. Ashmore, *Stiffness of sensory hair bundles in the sacculus of the frog.* Hear Res, 1986. 23(1): p. 93-104; Spoon, C., et al., *Steady-state stiffness of utricular hair cells depends on macular location and hair bundle structure.* J Neurophysiol, 2011. 106(6): p. 2950-63.) The blast exposure destroyed approximately one-third of the hair cells in the striola region of the saccule. Importantly, HK-2 treatment restored hair cell densities to normal levels similar to those measured in the BEP and BEPHK-2 groups.

Conclusion: Our blast trauma data extend and elaborate upon our earlier preclinical study showing that orally administered HK-2 not only protects against conventional NIHL induced by moderate intensity workday noise exposures, but also extremely intense blast wave exposures. HK-2, conveniently administered in rat chow, significantly reduced blast-induced OHC and IHC loss by ~67% and ~57% respectively. Our results show for the first time that HK-2 completely prevented the blast-wave induced degeneration of ANF and SGN out to at least 60 days post-exposure. Our blast exposure selectively destroyed approximately one-third of the vestibular hair cells located in the striola region of the sacculus but failed to cause hair cell degeneration in the marginal region of the sacculus, the striola and marginal regions of the utricle and hair cells in the ampulla of the three semicircular canals. The stability and ease of administration of HK-2 make it a promising candidate for human clinical trials among individuals routinely exposed to high levels of occupational and/or recreational noise such as military personnel, musicians and first responders. Because HK-2 passes through the blood-brain barrier, it has the potential to protect against many other sensory and neural injuries that arise from excessive or prolonged oxidative stress (e.g., concussion, drug toxicity, Alzheimer's, Parkinson's and aging).

The present methods may be better understood in view of the following examples.

Subjects. The twenty-four male Sprague-Dawley rats (Charles River Laboratories) in this study were ~12 weeks old at the start of the experiment. The rats were housed in the Laboratory Animal Facility at the University at Buffalo and given free access to food and water. The colony room was maintained at 22° C. with a 12-hour light-dark cycle. All procedures regarding the use and handling of animals were reviewed and approved by the Institutional Animal Care and Use Committee at the University at Buffalo.

Blast wave exposure. All rats were exposed to 6 blasts presented once every 5 minutes using equipment and procedures similar to those previously described. (See Manohar, S., et al., *Blast-induced hearing loss suppresses hippocampal neurogenesis and disrupts long term spatial memory.* Hear Res, 2020. 395: p. 108022; Stachowiak, M. K., et al., *Neurogenesis and Oligodendrogenesis in a Mouse Model of Blast-Induced Traumatic Brain Injury.* Neurology and Neurobiology, 2020: p. 1-14; and Newman, A. J., et al., *Low-cost blast wave generator for studies of hearing loss and brain injury: blast wave effects in closed spaces.* J Neurosci Methods, 2015. 242: p. 82-92.) Each rat was anesthetized with an intraperitoneal injection of ketamine (50 mg/kg) and xylazine (6 mg/kg) and stable anesthesia was maintained with supplementary half-doses of anesthetics as needed to maintain a stable anesthetic state. Each anesthetized rat was placed in a wire-mesh cage 5 cm with the snout of the rat facing the front of the blast tube opening. The average blast peak pressure level was 186 dB peak SPL (±0.8 dB, SEM, ~39.9 kPa). The intensity was selected based on our prior study in which we found no evidence of tympanic membrane or ossicular damage in rats exposed at 188 dB pSPL (Newman, A. J. et al.), consistent with an earlier report. (Roberto, M., R. P. Hamernik, and G. A. Turrentine, *Damage of the auditory system associated with acute blast trauma.* Ann Otol Rhinol Laryngol Suppl, 1989. 140: p. 23-34)

Experimental groups. The rats were divided into four groups (n=6/group): (1) Blast alone (B), (2) Blast plus earplugs (BEP), (3) Blast plus HK-2 (BHK-2) and (4) Blast plus earplugs plus HK-2 (BEPHK-2). All rats had free access to water and standard lab chow except for the BHK-2 and BEPHK-2 groups that also received HK-2 as noted below.

Earplugs. Both ear canals of rats in the BEP and BEPHK-2 groups were plugged with a thin wedge of foam cut from a commercial EARR earplug and then covered with petroleum jelly. This ear plugging methods was highly effective at preventing hair cells loss as reported in the Results.

HK-2 synthesis and administration. HK-2 was synthesized and evaluated for purity (>99%) as described previously. (Kawada, H. and P. F. Kador, *Orally Bioavailable Metal Chelators and Radical Scavengers: Multifunctional Antioxidants for the Coadjutant Treatment of Neurodegenerative Diseases.* J Med Chem, 2015. 58(22): p. 8796-805; U.S. Pat. No. 8,877,766 B2) Rats in the BHK-2 group and BEPHK-2 group were fed the same standard laboratory rat chow as the other two groups, however, the chow had been treated with HK-2 as described previously. (Chen, G. D., et al.; Manohar, S., et al., *Combined antioxidants and anti-inflammatory therapies fail to attenuate the early and late phases of cyclodextrin-induced cochlear damage and hearing loss.* Hear Res, 2022. 414: p. 108409.) HK-2 treated food was administered to rats starting 7-days prior to the blast wave exposure and continuing for 30-days following exposure. Based on the rat's daily food consumption, measured every 2 days together with body weight, the average oral consumption of HK-2 was ~50 mg/kg/day. (Id.)

Tissue preparation. Approximately 60-days after the blast wave exposure, the rats from all four groups were deeply anesthetized with ketamine (50 mg/kg, i.p.) and xylazine (6 mg/kg, i.p.) and decapitated. The temporal bones were quickly removed. Under a dissection microscope, openings were made in the cochlear apex, round window, and the oval window. Samples for surface preparations of the cochlear basilar membrane and vestibular end-organs were perfused with 10% formalin in phosphate buffered saline (PBS) into the cochlear and vestibular cavities and then immersed in the fixative overnight as described previously. (Manohar, S., et al. 2022; Ding, D., et al., *Spatiotemporal Developmental Upregulation of Prestin Correlates With the Severity and Location of Cyclodextrin-Induced Outer Hair Cell Loss and Hearing Loss.* Front Cell Dev Biol, 2021. 9: p. 643709.) Samples for temporal bone sections were fixed with 2.5% glutaraldehyde in 0.1M PBS for 6 h. After rinsing with PBS, samples were immersed in 2% osmium tetroxide in 0.1M PBS for 2 h. (Wang, J., D. Ding, and R. J. Salvi, *Carboplatin-induced early cochlear lesion in chinchillas.* Hear Res, 2003. 181(1-2): p. 65-72.)

After fixation, samples for surface preparations of the cochlea and vestibular end-organs were decalcified (Decalcifying solution-Lite, Millipore Sigma, D0818) for 48 h. Then, the cochlear basilar membrane, macula of saccule, macula of utricle, and three crista ampullae were dissected out under a dissecting microscope, stained with Harris hematoxylin solution, and mounted in glycerin on glass slides as described previously. (Ding, D., et al.)

Samples used for temporal bone sections were decalcified with 10% EDTA solution for 5 days, dehydrated through a graded series of ethanol solution ending at 100% and pure acetone as described previously. (Wang, J. et al.) The temporal bones were then embedded in Epon 812 resin. After high temperature polymerization, the temporal bones were cut parallel to the axis of the cochlear modiolus at a thickness of 3 m using an ultramicrotome (Reichert Supernova) equipped with glass knives. The semi-thin slices were collected on glass slides and stained with toluidine blue.

Cochlear hair cells. The hematoxylin-stained cochlear basilar membranes were examined with a light microscope (Zeiss Standard, 400× magnification). Cochlear IHC and OHC were counted along the entire length of the basilar membrane. A hair cell was counted as present if both the cuticular plate and nucleus were clearly visible and considered missing if either were absent. The cell counts were entered into a custom computer program to generate a cochleogram showing the percentages of missing OHC and IHC as a function of percentage distance from the apex of the cochlea based on laboratory norms as described previously. (Manohar, S. et al. 2022; Wang, J. et al. 2003) Cochlear location was related to frequency using a rat frequency-place map. (Muller, M. 1991) Mean cochleograms (n=6/group) were computed for each group as described previously. (Ding, D. et al. 2021; Ding, D., et al., *Hydroxypropyl-beta-cyclodextrin causes massive damage to the developing auditory and vestibular system*. Hear Res, 2020. 396: p. 108073.)

Auditory nerve fibers (ANF) in habenula perforata. Sections were taken from the Epon 812 embedded samples tangent to the habenula perforata as described previously. (Ding, D., H. Jiang, and R. Salvi, *Cochlear spiral ganglion neuron degeneration following cyclodextrin-induced hearing loss*. Hear Res, 2021. 400: p. 108125; Ding, L., S. L. McFadden, and R. J. Salvi, *Calpain immunoreactivity and morphological damage in chinchilla inner ears after carboplatin*. J Assoc Res Otolaryngol, 2002. 3(1): p. 68-79.) Sections were mounted on glass slides, stained with toluidine blue and examined under a light microscope (Zeiss Axioskop) at 200× magnification. Specimens were photographed with a digital camera (SPOT Insight, Diagnostic Instruments Inc.) and processed with imaging software (SPOT Software, version 4.6; Adobe Photoshop 5.5). For each experimental condition, the number of ANF was counted in each habenula perforata in the middle of the basal turn (~70%-distance-from-apex, 25 kHz region). Counts were obtained from 10 habenula perforata in the middle of basal turn and a mean value computed at that location for each animal. ANF counts were obtained from 6 cochleae per group.

Spiral ganglion neurons (SGN) in Rosenthal's canal. To quantify the number of SGN in sections, 3 μm thick serial sections were cut parallel to the axial axis of modiolus. Sections were mounted on glass slides, stained with toluidine blue, examined under a light microscope, photographed and processed using imaging software as described previously. (Ding, D. et al. 2020) For each cochlea, representative photomicrographs of Rosenthal's canal were obtained from the middle of basal turn (~25 kHz location). The number of SGN were counted in each section (every fifth section) of Rosenthal's canal. SGN counts were obtained from five separate sections from each animal and a mean value was computed. SGN counts were obtained from 6 cochleae per group.

Quantifications of vestibular hair cells. The hematoxylin-stained vestibular sensory epithelium of the macula of the saccule, macula of the utricle, and three crista ampullae were mounted in glycerin on glass slides as flat surface preparations. The samples were cover slipped and examined with a light microscope as described previously. (Ding, D. et al. 2020) Section were examined under a light microscope (1000×) and the number of vestibular hair cells were counted in a 0.0108 $mm^2$ region (see FIG. 5A). Hair cell counts were obtained from four regions in each vestibular sensory epithelium and a mean value was computed for each vestibular end-organ.

Analysis: GraphPad Prism (ver. 5) software was used to plot and analyze the results as described below.

Figure 1B:
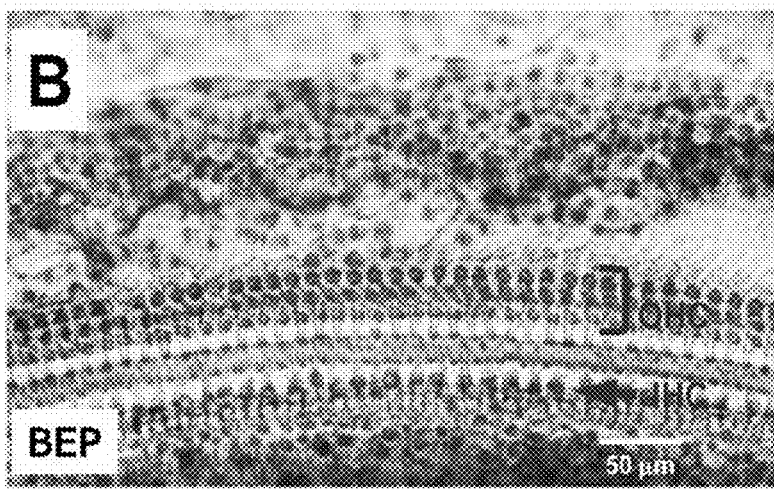
FIG. 1B depicts a representative photomicrograph of a surface preparation taken from the middle of the basal turn of the cochlea of a blast exposed rat fitted with earplugs.
Figure 1C:
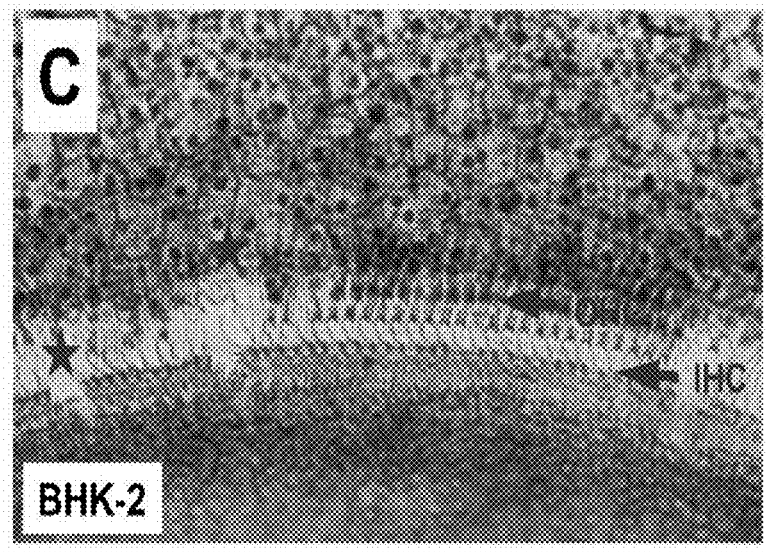
FIG. 1C depicts a representative photomicrograph of a surface preparation taken from the middle of the basal turn of the cochlea of a blast exposed rat treated with HK-2.
Figure 1D:
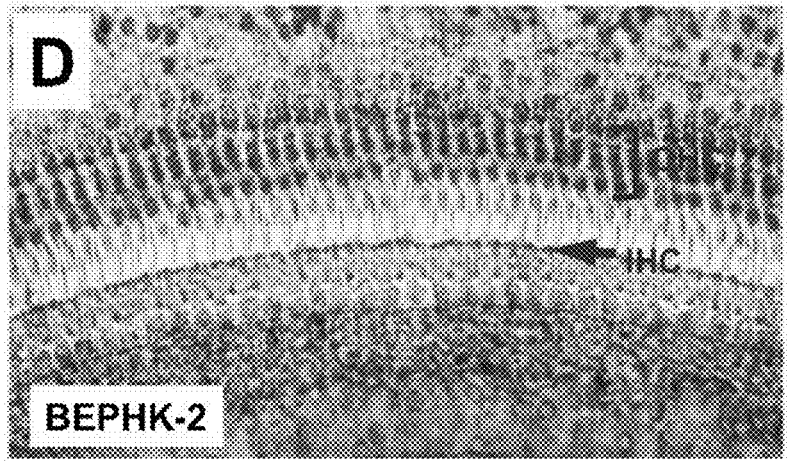
FIG. 1D depicts a representative photomicrograph of a surface preparation taken from the middle of the basal turn of the cochlea of a blast exposed rat fitted with earplugs and treated with HK-2.

Outer hair cells: To determine if HK-2 could protect cochlear hair cells from six blast exposures (186 dB peak SPL, once every 5-minutes), one cochlea from each of the rats in the four groups was evaluated along the entire length of the basilar membrane. The blast exposure damaged a large portion of the organ of Corti in the unprotected blast wave group. FIG. 1A shows a representative photomicrograph of a surface preparation taken from the middle of the basal turn of the cochlea of an untreated rat in the B group. Because the blast exposure destroyed all of the hair cells and support cells, the missing organ of Corti was replaced by a flattened epithelium comprised largely of cuboidal-shaped cells with a nucleus surrounded by pale cytoplasm (FIG. 1A, star). In similar blast-exposed rats fitted with earplugs (BEP), the hair cells and support cells remained largely intact as illustrated by the surface preparation of the organ of Corti in the middle of the basal turn (FIG. 1B). Three parallel rows of OHC and a single row of IHC were present along the length of the organ of Corti. Among the rats treated only with HK-2 in the BHK-2 group, patches of OHC and IHC were missing along the organ of Corti in the middle of the basal turn (FIG. 1C); damage was more extensive to OHC than IHC. Among the rats in the BEPHK-2 group fitted with earplugs and treated with HK-2, there was little or no evidence of OHC or IHC loss in the middle of the basal turn (FIG. 1D).

FIG. 1: HK-2 suppresses blast-induced hair cell loss. Representative photomicrograph of surface preparations from the middle of basal turn of the cochlea stained with Harris hematoxylin. Cochlea evaluated 2-months after exposure to 6 blasts of ~186 dB peak sound pressure level. Results from (A) blast-alone (B) group, (B) blast group with earplugs (B+E), (C) blast group treated with HK-2 (BHK-2) and (D) blast group treated with earplugs and HK-2 (BHK-2). Nearly all outer hair cells (OHC) and inner hair cells (IHC) are missing and replaced by large flat, cuboidal cells (panel A, stars). Nearly all OHC and IHC present in blasted-exposed rats treated with ear plugs (B) or earplugs combined with HK-2 (D). Surface preparations from blast-exposed rats treated with HK-2 (C) shows patches of missing hair cells and flattened epithelium (star) interspersed with regions where rows of OHC and IHC are present. Scale bar in panel B: 50 μm.

To quantify the results, cochleograms were prepared from one cochlea of each animal in each of the four groups. Mean percent OHC and IHC loss were determined over 20% intervals along the cochlea for each rat. These data were used to construct mean cochleograms (n=6/group, +/−SEM) for each group showing the percent OHC loss in 20% intervals from the apex to the base of the cochlea. Cochlear location was related to frequency using a rat tonotopic map. (Muller, M. 1991) FIG. 2A compares the mean OHC losses in the four groups. Mean OHC losses in the B group declined from ~100% near the high-frequency base of the cochlea to ~67% in the low-frequency apex. Mean OHC losses in the BEP group were substantially less than in the B group; OHC losses in the BEP group decreased from ~37% near the base of the cochlea to less than 9% near the apex. OHC losses in the BHK-2 group were also substantially less than in the B group. BHK-2 OHC loss was ~76% in the high-frequency base of the cochlea, declining to ~39% and then 10% at the 70% and 10% locations respectively. OHC losses in the BEPHK-2 group were nearly identical to those in the BEP group except in the extreme base where loss was about 10% less in the BEPHK-2 group. A two-way repeated measures analysis of variance of OHC loss revealed a significant treatment effect (F 3, 80=14.71, p<0.0001) and a significant effect of cochlear location (F 4, 80=14.57, p<0.0001). Bonferroni post-testing revealed significant differences in OHC loss between the B versus BEP groups (ear plug protective effect) at all cochlear locations (p<0.001); significant differences in OHC loss between the B versus BHK-2 groups (HK-2 protective effect) at cochlear locations of 10, 30, 70% (p<0.01) and 50% (p<0.05), and a significant difference in OHC loss between the BHK-2 versus BEPHK-2 groups at the 90% cochlear location (p<0.05).

FIG. 2: HK-2 prevents blast-induced loss of outer hair cells (OHC) and inner hair cells (IHC). Mean (n=6, +/−SEM) cochleograms for the B, BEP, BHK-2 and BEPHK-2 groups. Cochleogram shows percent (A) OHC loss and (B) IHC loss versus percent distance from the apex of the cochlea (20% intervals). Lower bar shows rat tonotopic map. (Muller, M. 1991) A two-way repeated measures analysis revealed a significant effect of treatment (p<0.0001) and cochlear location (p<0.0001); see text for details. Bonferroni post-test test revealed significant differences in the amount of OHC or IHC loss between B versus BEP group (#), B versus BHK-2 group (%), B+E versus BHK-2 group ($) and BHK-2 and BEPHK-2 group (&). 1, 2 and 3 symbols correspond to p<0.05, 0.01 and 0.001; see text for details.

Inner hair cells: The blast wave exposure caused extensive IHC damage. Mean IHC loss decreased from ~96% near the base of the cochlea, decreasing to ~80% near the middle of the cochlea and then declining to ~22% near the apex (FIG. 2B). IHC losses in the BEP group and BEPHK-2 group were minimal except for losses ~14-19% in base of the cochlea. Mean IHC losses in the BHK-2 were much less than in the B group particularly in the apical two-thirds of the cochlea. Mean IHC loss in the BHK-2 was ~67% near the base of the cochlea, declining to ~20 in the middle of the cochlea and then falling to 0% near the apex. A two-way repeated measures analysis of variance revealed a significant treatment effect (F 3, 80=16.35, p<0.0001) and a significant effect of cochlear location (F 4, 80=23.63, p<0.0001). Bonferroni post-testing revealed significant differences in IHC loss between the B versus BEP groups (ear plug protective effect) at 30%, 50%, 70% and 90% cochlear locations (p<0.001); significant differences in IHC between the B versus BHK-2 groups (HK-2 protective effect) at cochlear locations of 30, 50 and 70% (p<0.001), a significant difference in IHC between BEP and BHK-2 groups at the 90% location (p<0.01) and a significant difference in IHC loss between the BHK-2 versus BEPHK-2 group at the 90% cochlear location (p<0.01).

FIG. 3: HK-2 suppresses blast-induced loss of auditory nerve fibers (ANF). Representative photomicrographs of toluidine blue stained, 3 μm sections from middle of basal turn of cochlea. Data obtained 2-months after exposure to 6 blasts of ~186 dB peak sound pressure level. Results showing habenula perforata in (A) B group, dashed circle (25 μm scale bar), (B) BEP group, (C) BHK-2 group, and (D) BEPHK-2 group. (E) High magnification view of toluidine blue stained ANF in habenula perforata. ANF characterized by darkly stained ring surrounding pale cytoplasm (arrowhead). (F) Mean (n=6, +/−SEM) number of ANF per habenula perforata in B group is significantly less (p<0.001) than in BEP group, BHK-2 group and BEPHK-2 group; see text for details.

Figure 3A:
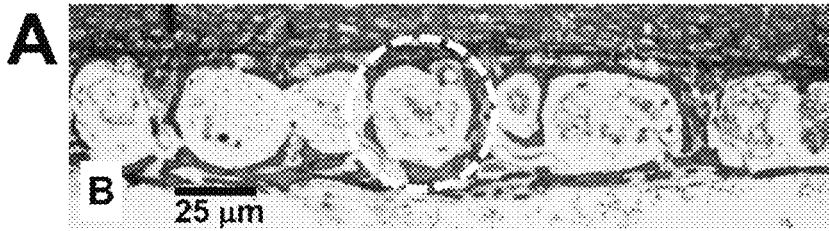
FIGS. 3A-3D show views of the habenula perforata from untreated blast exposed rats (3A), blast exposed rats protected with earplugs (3B), blast exposed rats treated with HK-2 (3C), blast exposed rats fitted with earplugs and treated with HK-2 (3D).
Figure 3B:
Figure 3C:
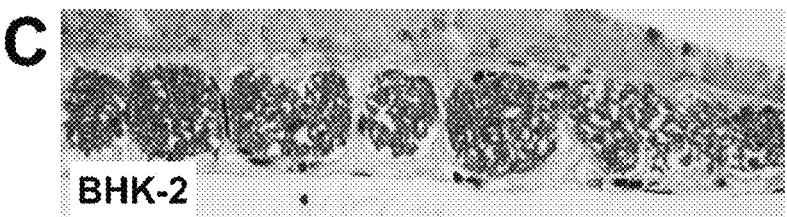
Figure 3D:
Figure 3E:
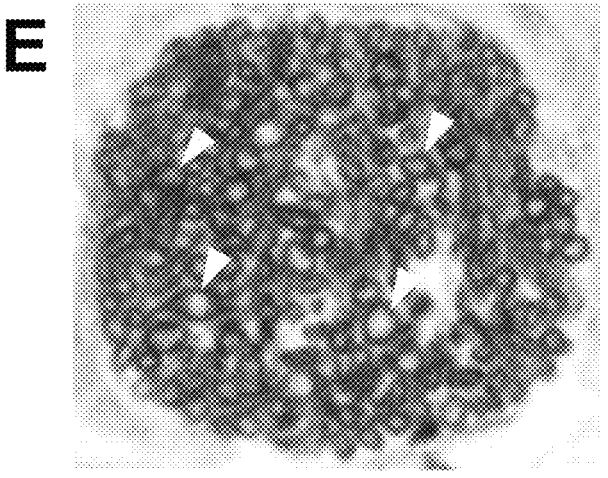
FIG. 3E shows a higher magnification view of the habenula perforata from a blast exposed rat protected with earplugs.
Figure 3F:
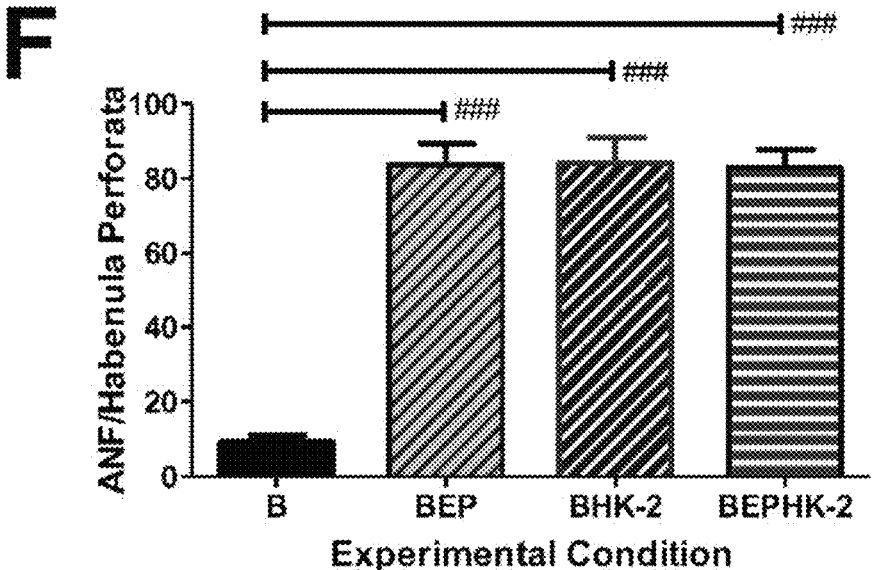
FIG. 3F shows a graph comparing the ANF loss in blast exposed rats (B) to the ANF loss in blast exposed rats fitted with earplugs (BEP), treated with HK-2 (BHK-2), and fitted with earplugs and treated with HK-2 (BEPHK-2).

Auditory nerve fibers: Large IHC losses are often accompanied by ANF degeneration. (Bohne, B. A. 2017) To quantify the degree of ANF degeneration, we counted the number of ANF in the habenula perforata in the middle of the basal turn of the cochlea (~25 kHz location). A massive loss of ANF was evident in the habenula perforata of rats in the B group as illustrated by the representative photomicrograph in FIG. 3A. In contrast, the habenula perforata was filled with ANF in the BEP, BHK-2 and BEPHK-2 groups. FIG. 3E shows a high magnification view of the habenula perforata from a rat in the BEP group. The ANF in the habenula perforata were characterized by a darkly stained ring surrounding a lightly stained cytoplasmic interior (arrowheads). Counts were made of the number of ANF in each habenula perforata (see Methods), the mean number of ANF was determined for each rat and the data used to compute the mean number of ANF per habenula perforata (n=6, +/−SEM) for each group. The mean number of ANF/habenula perforata was ~9.2 in the blast alone group (B) versus 83.7, 84.2 and 82.8 in the BEP, BHK-2 and BEPHK-2 groups, respectively. There was a significant difference across groups (one-way analysis of variance, F 3, 20=52.45, p<0.0001). The number of ANF/habenula perforata in the B group was significantly less (Newman-Keuls Multiple comparison) than in the BEP (p<0.05), BHK-2 group (p<0.05) and BEPHK-2 group (p<0.05). There were no significant differences among the BEP, BHK-2 and BEPHK-2 groups. Thus, HK-2 provided complete protection against blast-induced ANF degeneration, protection equal to BEP and BEPHK2.

Figure 4A:
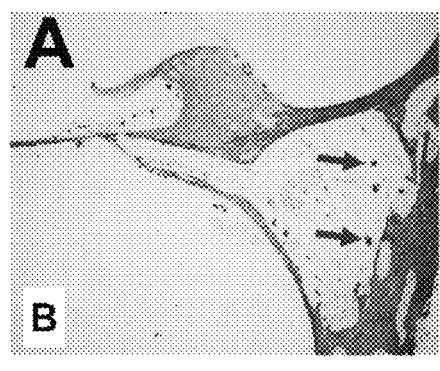
FIGS. 4A-4D show views of the Rosenthal's canal from untreated blast exposed rats (4A), blast exposed rats protected with earplugs (4B), blast exposed rats treated with HK-2 (4C), blast exposed rats fitted with earplugs and treated with HK-2 (4D).
Figure 4B:
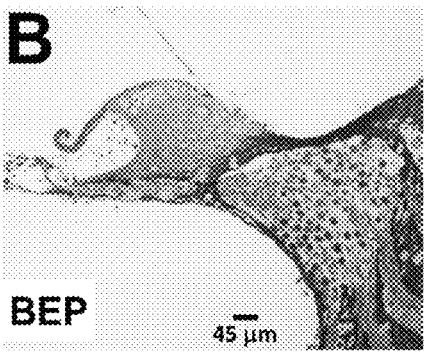
Figure 4C:
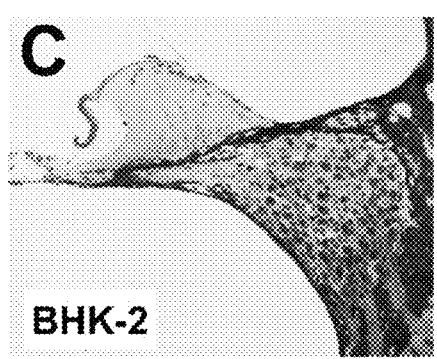
Figure 4D:
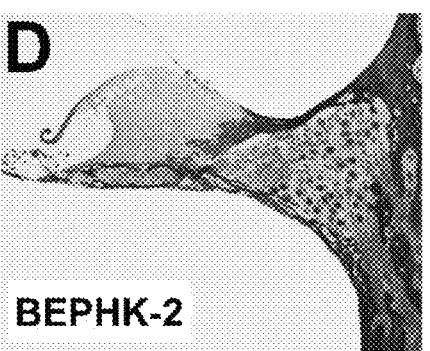
Figure 4E:
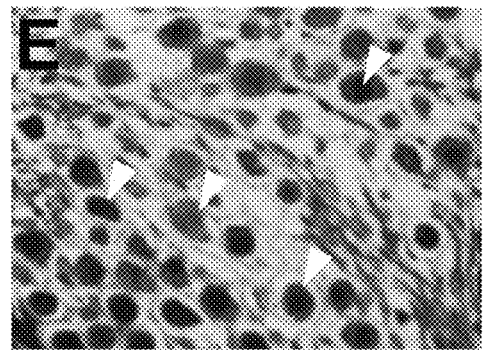
FIG. 4E shows a higher magnification view of the Rosenthal's canal from a blast exposed rat protected with earplugs.

Spiral ganglion neurons: The noise-induced destruction of many IHC generally results in the loss of SGN. To determine the extent of blast-induced neural degeneration, we counted the number of SGN in radial sections from the middle of the basal turn of the cochlea (~25 kHz location). FIGS. 4A-D show representative cross of Rosenthal's canal from rats in the experimental groups. Rosenthal's canal in the B group was largely devoid of SGN except for a few lone survivors (FIG. 4A). In contrast, Rosenthal's canal in the BEP, BHK-2 group and BEPHK-2 group were filled with SGN. FIG. 3E shows a high magnification view of Rosenthal's canal from a rat in the BEP group. SGN were characterized by a darkly stained nucleus surrounded by lightly stained cytoplasm (arrowheads). Counts were made of the number of SGN in each cross section (see Methods for details) and the mean number of SGN per section was determined for each cochlea. The individual data were used to determine the mean (n=6, +/−SEM) number of SGN/section in each group. The mean number of SGN per section was ~9 in the B group versus 42.8, 42.3 and 41.8 in the BEP, BHK-2 and BEPHK-2 groups, respectively. There was a significant difference across groups (one-way analysis of variance, F 3, 20=62.32, p<0.0001). The number of SGN/section in the B group was significantly less (Newman-Keuls Multiple comparison) than in the BEP group (p<0.05), BHK-2 group (p<0.05) and BEPHK-2 group (p<0.05); there were no significant differences among these three groups. These results show that HK-2 provided significant protection against blast-induced SGN degeneration, protection equal to EP alone and EP+HK2.

FIG. 4: HK-2 attenuates blast-induced degeneration of spiral ganglion neurons (SGN) in Rosenthal's canal. Representative photomicrograph of toluidine blue stained sections from the middle of the basal turn of cochlea (25 kHz location) 2-months after exposure to 6 blasts of ~186 dB peak sound pressure level. Sections from (A) B group, (B) B+E group, (C) BHK-2 group, and (D) BEPHK-2 group. Arrows in FIG. 4A point to a few surviving SGN in Rosenthal's canal. (E) High magnification view of toluidine blue stained SGN soma (arrowheads). (F) Mean (n=6, +/−SEM) number of SGN per section in B group significantly less (###, p<0.001) than in BEP group, BHK-2 group and BEPHK-2 group; see text for details.

Saccule hair cell densities in striola and marginal regions: Because blast wave exposures reportedly damage vestibular hair cells (Akin, F. W. et al. 2017; Lien, S. and Dickman, J. D. 2018), we measured hair cell densities in the macula of the saccule, utricle and the crista ampullae of the three semicircular canals. FIG. 5A shows a representative photomicrograph of a surface preparation of the maculae of the saccule from a rat in the BEP group. Vestibular hair cells in the BEP group were densely packed throughout the epithelium and were characterized by darkly-stained nucleus surrounded by pale cytoplasm. In the striola region of the saccule (FIG. 5B), vestibular hair cell density was greatly reduced in a large stripe surrounded by circular patches of missing hair cells. In contrast, vestibular hair cell density in the surrounding marginal region of the saccule appeared normal.

FIG. 5: HK-2 reduces blast-induced degeneration of vestibular hair cells in saccule. (A-B) Representative photomicrographs of surface preparations of saccule in vicinity of striola; specimens stained with Harris hematoxylin. (A) Representative photomicrograph of saccule obtained from rat in the BEP group two months post-blast. White arrowheads point to darkly stained nuclei of vestibular hair cells surrounded by lightly stained nerve terminals. Number of vestibular hair cells counted in 0.12×0.09 mm areas (0.0108 mm$^2$) in striola and marginal regions of saccule. (B) Representative photomicrograph from saccule of rat in blast exposed group (B) two months post-exposure. Many hair cells missing (arrows) from center of striola and in adjacent circular patches in contrast to high density of vestibular hair cells in marginal area. (C) Mean (n=6, +/−SEM) hair cell density in striola region of saccule. Hair cell density in the B group is significantly less than in BEP group (p<0.001), the BEPHK-2 group (p<0.001) and the BHK-2 group (p<0.01).

Vestibular hair cell densities were measured in the striola and marginal regions of the saccule of each animal (see details in Methods) and mean (n=6, +/−SEM) hair cell densities were computed for each group. Mean vestibular hair cell densities in the striola of the BEP, BHK-2 and BEPHK-2 groups were 109.8, 102.7 and 112.0 hair cell/0.0108 mm$^2$ respectively versus 71.83 hair cells/0.0108 mm$^2$ in the B group, about 35% less than the other three groups. A one-way analysis of variance revealed a significant difference in hair cells density across groups (F 3, 20=24.35, p<0.0001). Bonferroni post-testing indicated that striola hair cell density in the B group was significantly less than in the BEP (p<0.05), BHK-2 (p<0.05) and BEPHK-2 groups (p<0.05). However, striola hair cell densities were not significantly different from one another in the BPEP, BHK-2 and BEPHK-2 groups. FIG. 5D shows the mean (n=6, +/−SEM) hair cell densities in the marginal region of the saccule for the four experimental groups. Mean hair cell densities in the marginal cell region of the saccule were 122.8, 122.7, 122.2 and 123.0/0.0108 mm$^2$ for the B, BEP, BHK-2 and BEPHK-2 group, respectively. A one-way analysis of variance revealed no significant difference in marginal hair cell densities across the four groups (F 3, 20=0.037, p=0.9901). Thus, HK-2 provided significant protection against blast-induced hair cell loss in the striola of the saccule; a protective effect equivalent to that provided by earplugs alone.

Figure 6A:
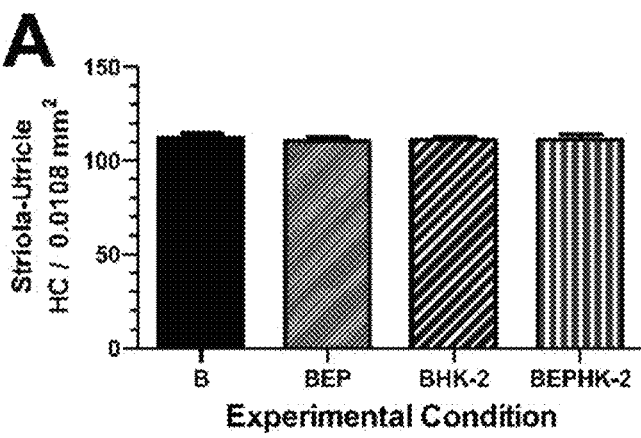
FIG. 6A depicts a graph illustrating damage to the Striola-Urticle under various experimental conditions.
Figure 6B:
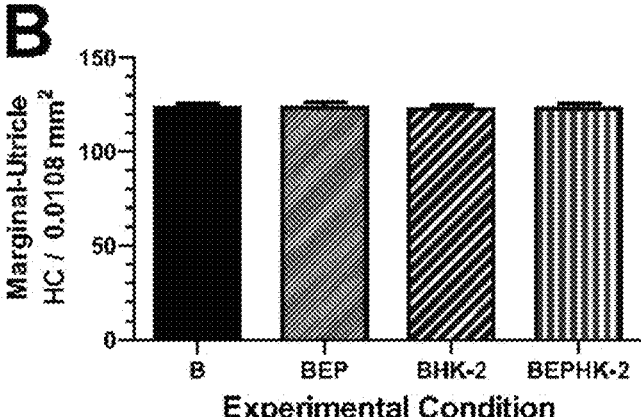
FIG. 6B depicts a graph illustrating damage to the Marginal-Urticle under various experimental conditions.

Utricle and ampullae hair cell densities: Hair cell densities were also evaluated in the macula of the utricle and cristae ampullae of the three semicircular canals. There was no apparent loss of hair cells in the macula of the utricle. Mean hair cell densities in the striola region of the macula of the utricle were 112.2, 110.2, 111.0 and 111.3/0.0108 mm$^2$ for the B, BEP, BHK-2 and BEPHK-2 groups respectively (FIG. 6A, n=6/group, +/−SEM), values similar to those seen in normal controls. There was no significant difference between groups (one-way analysis of variance, F 3, 20=0.146, p=0.931). Mean hair cell densities in the marginal region of the macula of the utricle were 123.3, 123.5, 122.7 and 122.8/0.0108 mm$^2$ for the B, BEP, BHK-2 and BEPHK-2 groups respectively (FIG. 6A, n=6/group, +/−SEM), values within the normal range. There was no significant difference between groups (one-way analysis of variance, F 3, 20=0.028, p=0.993). Mean hair cell densities in the crista of the ampulla of the three semicircular canals were 122, 121.3, 121.8 and 122.8/0.0108 mm$^2$ for the B, BEP, BHK-2 and BEPHK-2 groups respectively (FIG. 6A, n=18, 6/experimental group, +/−SEM). There were no significant differences between groups (one-way analysis of variance, F 3, 20=0.3626, p=0.78). Taken together, these results indicate that blast wave induced vestibular hair cell loss was confined to the striola region of the saccule.

Figure 6C:
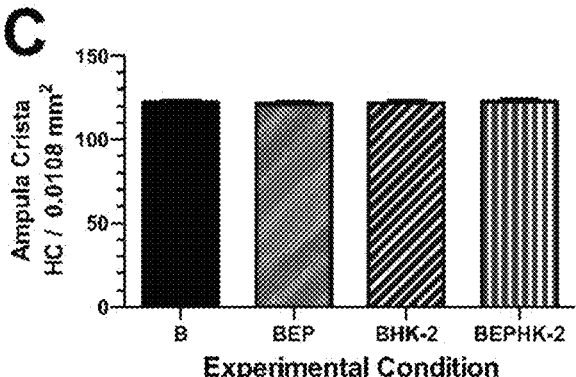
FIG. 6C depicts a graph illustrating damage to the Ampula Crista under various experimental conditions.

FIG. 6: Blast wave exposure did not alter hair cell densities in the striola and marginal regions of the utricle and the ampulla of three semicircular canals. (A) Mean (n=6, +/−SEM) vestibular hair cell densities (HC/0.0108 mm$^2$) in the striola region of the utricle; note nearly identical values across B, BEP, BHK-2 and BEPHK-2 experimental groups. (B) (A) Mean (n=6, +/−SEM) vestibular hair cell densities (HC/0.0108 mm$^2$) in the marginal region of the utricle were nearly identical across B, BEP, BHK-2 and BEPHK-2 experimental conditions. (C) Mean (n=18, +/−SEM) vestibular hair cell densities (HC/0.0108 mm$^2$) in ampulla of crista of three semicircular canals (n=6/canal) nearly identical across B, BEP, BHK-2 and BEPHK-2 experimental conditions.

It is to be understood that the method of preventing blast-induced loss of cochlear and vestibular hair cells and auditor spiral ganglion neurons is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preventing blast-induced hearing loss, comprising orally administering a composition comprising HK-2 to a subject in need thereof; wherein the subject's risk of developing blast-induced hearing loss results from the subject being exposed to at least one blast of about 186 dB.

2. The method of claim 1, wherein the subject is at an increased risk of exposure to an acoustic blast wave.

3. The method of claim 1, further comprising a reduction in the loss of cochlear hair cells.

4. The method of claim 1, further comprising a reduction in the loss of vestibular hair cells.

5. The method of claim 1, further comprising a reduction in the loss of auditory spiral ganglion neurons.

6. The method of claim 1, wherein the HK-2 is administered to the subject daily.

7. The method of claim 6, wherein the HK-2 is administered to the subject daily for a period of 30 days.

8. The method of claim 1, wherein the HK-2 is administered at a dose of about 50 mg per kg per day.

9. A method of preventing blast-induced hearing loss, comprising orally administering a composition comprising HK-2 to a subject in need thereof; wherein the subject was previously exposed to a blast wave of about 186 dB.

10. The method of claim 9, further comprising a reduction in the loss of auditory spiral ganglion neurons.

11. The method of claim 9, further comprising a reduction in the loss of cochlear hair cells.

12. The method of claim 9, further comprising a reduction in the loss of vestibular hair cells.

13. The method of claim 9, wherein the HK-2 is administered to the subject daily.

14. The method of claim 13, wherein the HK-2 is administered to the subject daily for a period of 30 days.

15. The method of claim 9, wherein the HK-2 is administered at a dose of about 50 mg per kg per day.

* * * * *